(12) United States Patent
Morgan

(10) Patent No.: US 6,200,345 B1
(45) Date of Patent: Mar. 13, 2001

(54) LOCKING TAPER ATTACHMENT SYSTEM HAVING IMPROVED BACTERIAL SEAL

(75) Inventor: Vincent J Morgan, Boston, MA (US)

(73) Assignee: Diro, Inc., Boston, MA (US)

( * ) Notice: Subject to any disclaimer, the term of this patent is extended or adjusted under 35 U.S.C. 154(b) by 0 days.

(21) Appl. No.: 09/341,100

(22) PCT Filed: Jan. 15, 1998

(86) PCT No.: PCT/US98/01169
§ 371 Date: Jul. 2, 1999
§ 102(e) Date: Jul. 2, 1999

(87) PCT Pub. No.: WO98/31300
PCT Pub. Date: Jul. 23, 1998

Related U.S. Application Data

(60) Provisional application No. 60/036,121, filed on Jan. 18, 1997.

(51) Int. Cl.[7] .......................................................... A61F 2/18
(52) U.S. Cl. .............................................. 623/10; 433/173
(58) Field of Search ................................... 623/10, 11.11; 433/167, 173, 225

(56) References Cited

U.S. PATENT DOCUMENTS

| 4,738,623 | * | 4/1988 | Driskell | 433/173 |
| 5,549,475 | * | 8/1996 | Duerr | 433/173 |
| 5,556,280 | * | 9/1996 | Pelak | 433/172 |

* cited by examiner

*Primary Examiner*—Michael J. Milano
(74) *Attorney, Agent, or Firm*—John A. Haug

(57) ABSTRACT

A first member (10,10',10") has a bore formed with a self holding taper which receives the post of a second member (14,14',14") formed with a matching self holding taper. A bacterial/endotoxin-seal is provided by having a portion of either the bore, contiguous to its mouth, or the post, at a location which corresponds to the location of the mouth of the bore when in the locked position, provided with a sealing taper (10c,16c) with a different angle selected to form an interference fit. The sealing taper (10c,16c) extends only along a minor portion of the longitudinal axis of the respective bore and post. The first member (10,10',10") is provided with an outer surface to promote osseointegration when used in bony sites.

10 Claims, 2 Drawing Sheets

LOCKING TAPER ATTACHMENT SYSTEM HAVING IMPROVED BACTERIAL SEAL

This application is a 371 of PCT US98/01169 filed Jan. 15, 1998 and claims benefit of Ser. No. 60/036,121 filed Jan. 18, 1997.

FIELD OF THE INVENTION

This invention relates generally to medical and dental attachment devices and more particularly to attachment devices utilizing a locking of self holding taper for use with medical orthopedic and dental osseointegration applications, such as spinal prosthetics or appendages, for example, toes, thumbs, ears, eyes and the like, and dental implants as well as non-osseointegrated, subcutaneous medical uses, for example, pump systems, catheters, and the like.

BACKGROUND OF THE INVENTION

It is known that prosthetic appendages, such as toes, thumbs, ears, eyes and the like, can be attached to a bone by using one of more attachment devices in the form of implants surgically positioned in recesses formed in the bone. One known system uses a type of implant having a threaded bore which is adapted to receive a threaded post of an abutment. The abutment in turn mounts the prosthesis. Although considerable success has been achieved with this system there is an inherent problem in that there is a certain space which must be provided between the male and female threads of a threaded system to which endotoxins and bacteria can find access.

This problem can be greatly diminished by using a locking or self holding taper arrangement for the implant bore and post member since a tighter fit is obtained. Such an arrangement is disclosed for dental applications in U.S. Pat. No. 4,738,623, the subject matter of which is incorporated herein by this reference. In recent years this system has come into wide use. In accordance with the patent, a dental implant of root member is surgically positioned within the mandibular of maxillary alveolar bone of a patient and, after healing, is fitted with a tooth-simulating prosthesis or crown. The root member is formed of biocompatible material, such as titanium, and is provided with multiple, outwardly extending fins to promote osseointegration with the alveolar bone. The implant is provided with a bore having a locking taper extending through the crestal end thereof. A permanent abutment member having a post portion, also formed with a locking taper, is mounted on the implant. The abutment member has an upstanding exterior surface adapted for mounting the prosthesis crown or denture and a basal portion having a spherical surface which extends through the gingiva and alveolar crest toward the implant.

Even though a tighter fit is obtained with a locking taper arrangement as described above, due to manufacturing tolerances it is possible for the taper of the post and the bore to be such that locking engagement occurs at the distal end of the post with the inner part of the bore thereby leaving a small annular crease available for endotoxins and/or bacteria cultures at the mouth of the implant. Due to the nature of the vascular supply of the mouth this phenomenon is not normally of great concern however, it is a significant concern where the application involves going through the epidermis.

SUMMARY OF THE INVENTION

It is an object of the present invention to provide a medical and dental attachment system having an improved bacterial and endotoxin seal for osseointegration members, such as dental implants and body appendages as well as non-osseointegrated subcutaneous medical uses. Another object is the provision of medical and dental attachment devices which overcome the above noted prior art limitations.

Briefly described, a system for anchoring a component in a living body made in accordance with the invention comprises a first member having a bore through a crestal end and a second member having a post section receivable in the bore where both the bore and the post are formed with a locking or self holding taper of a selected angle along a major portion of the length of the bore and post section and a minor portion of the length of one of the bore and post section having a different angle selected to cause an interference fit thereby providing a bacterial and endotoxin seal between the first and second members. The first member is preferably formed with a narrow annular rim circumscribing the bore, the rim having a thickness at its distal end portion as little as approximately 0.25 mm. The minor portion, having a seal portion with a different angle, is approximately 1 mm in length. In one embodiment, the minor portion is located contiguous to the entrance to the bore and has an angle less than the taper angle of the major portion of the bore. In another embodiment, the minor portion is located on the post section and has a seal angle greater than the taper angle of the major portion of the post section. When used in osseointegration applications the first member is formed with an outer surface configuration which includes structure to promote osseointegration, such as outwardly extending fins.

Additional objects, advantages and features of the novel and improved attachment system of this invention will be set forth in part in the description which follows and in part will be obvious from the description.

BRIEF DESCRIPTION OF THE DRAWINGS

The accompanying drawings, which are incorporated in and constitute a part of the specification, illustrate preferred embodiments of the invention and, together with the description, serve to explain the objects, advantages and principles of the invention. Dimensions may have been altered for the purposes of illustration. In the drawings.

DETAILED DESCRIPTION OF PREFERRED EMBODIMENTS

Figure 1:
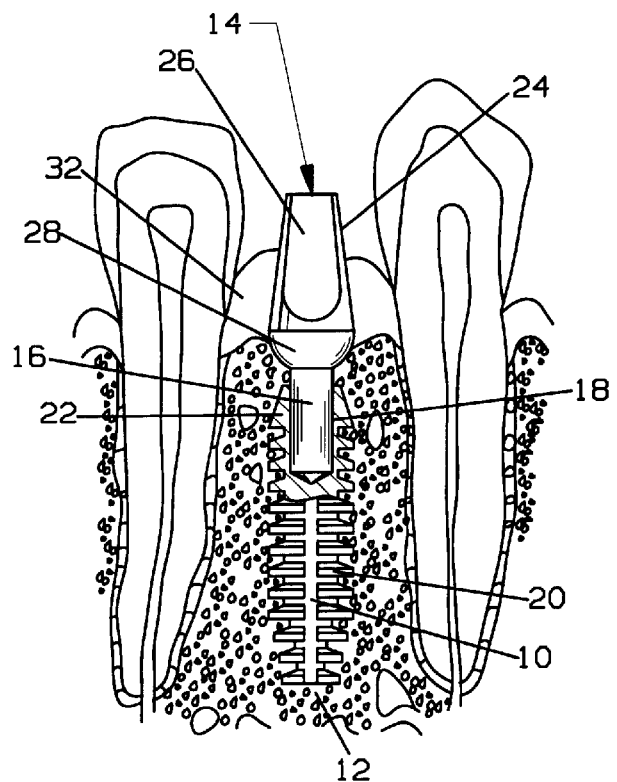
FIG. 1 is an enlarged elevational view, partly in cross section, of a root member implanted in the alveolar ridge with an abutment member mounted thereon according to the prior art.

With regard to FIG. 1, a root member or implant 10 is shown implanted in the alveolar bone 12 of a patient in the manner taught in U.S. Pat. No. 4,738,623, referenced above.

Head or abutment member 14 is mounted on the root member by means of a post 16 having a locking taper received in socket or bore 18 of root member 10, the bore having a matching locking taper. The root member has a plurality of outwardly extending fins formed in the lower portion thereof to promote osseointegration and a narrowed upwardly and inwardly contoured shoulder 22 formed above the fins.

Abutment member 14 has an upstanding, generally tapered, frusto-conical exterior surface 24 with an anti-rotational flat surface 26 for mounting a prosthetic crown and a basal portion 28 having a convex, frusto-spherical exterior surface which extends downwardly from the tapered portion. The center of the sphere which defines the frusto-conical surface lies on the axis of the frusto-conical surface so that the frusto-spherical and frusto-conical surfaces intersect along a circle. The frusto-spherical surface is disposed on a seat formed in the alveolar crest with post 16 extending into socket 18 and locked therein.

Figure 2:
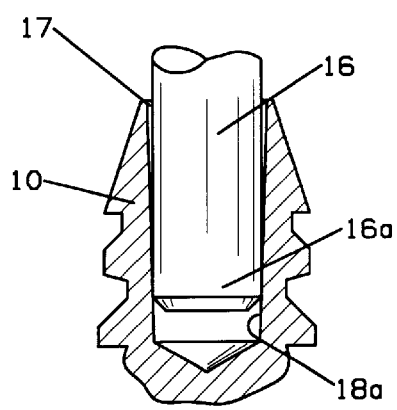
FIG. 2 is a broken away portion of FIG. 1.
Figure 3:
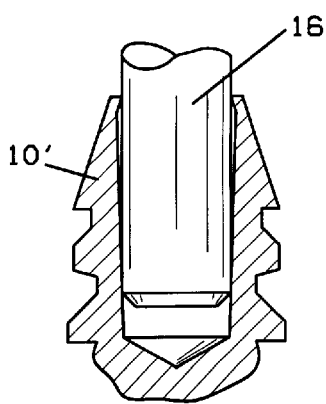
FIG. 3 is a view similar to FIG. 2 but showing the root member formed in accordance with a first embodiment of the invention.
Figure 4:
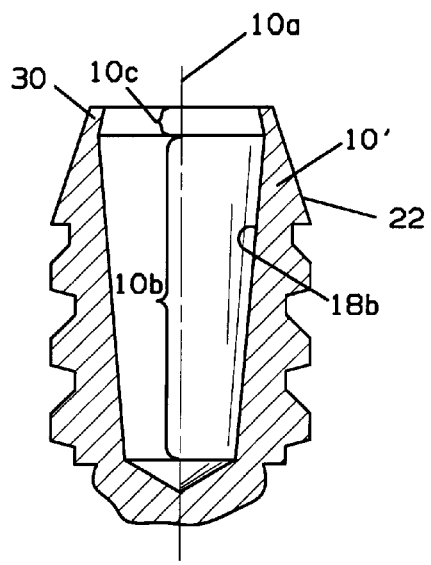
FIG. 4 is a cross sectional view of a broken away portion of the FIG. 3 root member.

The tapered post 16 and bore 18 are manufactured within close tolerances however, as shown in FIG. 2, it is possible, for example, when the bore has the largest allowed taper angle in the tolerance range and the post has the smallest allowed taper in the tolerance range for locking engagement to occur at the distal end 16a of the post at the inner end 18a of the bore at a relatively rigid portion of implant 10 thereby leaving a relatively small annular crease 17 at the mouth of the implant. This crease can serve as a site for a bacteria culture and/or endotoxins. In order to prevent this possibility, as shown in FIGS. 3 and 4, according to a first embodiment of the invention, the locking taper 18b extends along the major portion 10b of the length of the bore 18 with a seal portion 18c having a different angle formed in bore 18 along a minor portion 10c of the length of the bore 18 and located at the mouth of the bore, i.e., at the crestal end of implant 10. The angle of the seal portion 18c is selected to be less than that of taper 18b and preferably forms a slightly reverse or negative taper relative to that of taper 18b as shown in FIGS. 3 and 4 which have been somewhat exaggerated in the drawing for the purpose of illustration, to thereby form an interference fit. That is, the diameter of the bore increases in a direction going away from the crestal end toward the inner part of the bore along the minor portion of the length of the bore while the diameter of bore 18 along the major portion 18d is positive or decreases in that direction. Preferably, shoulder 22 forms a narrow annular rim 30, for example approximately 0.25 mm between bore 18 and shoulder 22 for a longitudinal distance corresponding to the minor portion enabling the rim to deflect slightly around the circumference of the bore and provide a tight bacterial and endotoxin seal totally eliminating any chance of an opening occurring at the mouth of the bore. The minor portion need only be approximately 1 mm, or even less, to be effective.

Figure 5:
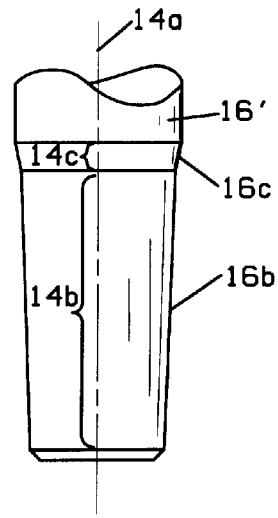
FIG. 5 is a front elevational view of a portion of the post section made in a accordance with another embodiment of the invention.

Alternatively, according to a modified embodiment, the sealing portion of the taper can be formed on post 16' as shown in FIG. 5. Locking taper 16b', matching that of the locking taper of bore 18 is provided along the major length 14b as measured along the longitudinal axis 14a of post 16 while sealing taper 16c is formed along the minor length 14c at a location corresponding to the mouth of bore 18 when inserted in the bore. The angle of sealing taper 16c in the FIG. 5 embodiment is selected to be slightly greater than the angle of locking taper 16b so that it will engage the narrow annular rim 30 creating an interference fit. Preferably, the differential between the angles is approximately 3 to 7 degrees and the thickness of the rim is approximately 0.25 mm or less for a longitudinal length equivalent to the longitudinal length of the minor portion, i.e., approximately 1 mm to provide the improved seal without impeding the ability of the post and implant to lock together.

The improved seal prevents the possibility of bacteria cultures in an area which can not be effectively cleaned or reached by blood-borne antibodies which otherwise would prevent infection in the implant site. The invention also serves to increase the area of engagement between the mating parts to thereby enhance pull-out resistance for certain tolerance combinations. That is, in situations where the angle of the taper in the bore is the maximum and the angle of the taper of the post is the minimum of the permitted tolerance range. Yet another advantage is that the invention obviates the possibility of any wobble with a pivot point below the mouth of the bore thereby providing greater stability, strength and fatigue resistance.

As mentioned above, implants adapted for osseointegration, in addition to dental uses, are also being used in orthopedics for fixation, e.g., spinal, or for various body appendages such as toes, thumbs, ears and eyes, by way of example. As in the case of dental implants, one or more recesses are formed in a bony site and a root member having an osseointegration promoting outer surface is placed in each recess. After a suitable healing period an abutment is mounted in each recess and a prosthesis is then mounted in the abutment. A prior art system employs an abutment having a threaded post member in combination with a threaded bore in the root member. As mentioned above, a problem associated with this system is that the screw threads inherently have a certain amount of space between the male and female threads which can serve as a site for bacteria and endotoxins and can result in infection and inflammation.

Figure 6:
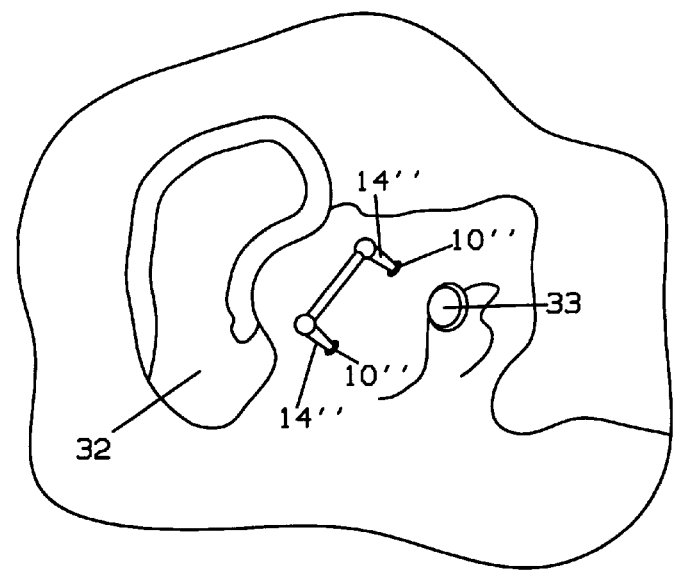
FIG. 6 is a blown apart view of a prosthetic ear and site prepared to receive the prosthesis using attachment devices made in accordance with the invention.

In accordance with another embodiment of the invention an implant and abutment system utilizing a locking or self holding taper with an improved seal portion as set forth in FIGS. 3–5 is used for attaching a prosthesis such as an ear shown by way of example in FIG. 6. Root members 10", only 3 or 4 mm in length are placed in the bone adjacent the ear canal. After a suitable healing period and abutment 14" is received in the bore of each root member. The ear prosthesis 32, formed of suitable material such as silicon, is then attached to the abutments in any suitable manner, as by use of clips engageable with a bar 34 mounted between two abutments. The abutments and bar assembly can be of the type described in commonly assigned U.S. Pat. No. 5,484,285, the subject matter of which is incorporated herein by this reference and to which further details may be had. In that patent a bar is shown extending between transversely extending bores in the head portions of spaced abutments. As described, the assembly is particularly adapted for use as an overdenture bar. In the present embodiment, the taper and seal portion of the abutment posts and the root member bores is the same as that shown in FIGS. 3–5 to provide an interference fit at the mouth of the bores and thereby provide an improved bacterial and endotoxin seal. It will be understood that the locking taper arrangement with the improved bacterial seal can be used for various other body appendages, such as toes, thumbs, noses, eyes and the like to provide an attachment system which is less susceptible to infection than prior art systems.

Although the above embodiments show the locking taper attachment system used with implants having an outer surface specifically adapted for osseointegration in a bone site it will be understood that the invention can also be used in various other applications including subcutaneous ones such as catheters, pumps and the like where it is desired to attach separate parts together. One or more bores with locking or self holding tapers can be formed directly in one of the parts and a mating part can be provided with a corresponding number of posts having matching locking or self holding tapers and, as in the above embodiments, with either the bores or the posts provided with the bacterial seal. The invention can be used in all medical and dental applications where endotoxins and bacteria would be problematic. Additionally, it can be used in industrial applications where a clean connection is desirable, such as in the scientific instrumentation, food processing industries, and the like.

Although the invention has been described with regard to specific preferred embodiments thereof, variations and modifications will become apparent to those skilled in the art. It is therefore the intention that the appended claims be interpreted as broadly as possible in view of the prior art to include all such variations and modifications.

What is claimed:

1. A system for anchoring a component within a body comprising a first member having a crestal end, a bore having a selected length along a longitudinal axis formed in the member through the crestal end, a second member comprising a post having a selected length dimensioned to be received in the bore of the first member, the bore having a self holding taper of a selected angle formed along a major portion of the length thereof, the post having a self holding taper of a matching angle formed along a major portion of the length thereof, a minor portion of the length of one of the bore and the post having a taper of a different angle to cause an interference fit to thereby provide a bacterial seal between the first and second members.

2. A system according to claim 1 in which the first member has a smooth surfaced shoulder extending from the bore at the crestal end with a narrow rim between the shoulder and the bore.

3. A system according to claim 2 in which the rim has a distal free end having a thickness of approximately 0.25 mm.

4. A system according to claim 1 in which the minor portion of the length of the bore and the post is approximately 1 mm in length.

5. A system according to claim 1 in which said minor portion of the length of the bore and post is located at the mouth of the bore.

6. A system according to claim 5 in which the angle of the taper of the minor portion is less than the angle of the taper of the major portion of the bore.

7. A system according to claim 6 in which the taper of the minor portion of the bore is negative with the diameter of the bore increasing in a direction going away from the crestal end and the taper of the minor portion of the bore is positive with the diameter of the bore decreasing in a direction going away from the crestal end.

8. A system according to claim 1 in which said minor portion of the length of one of the bore and the post is located on the post.

9. A system according to claim 8 in which the angle of the taper of the minor portion of the second member is greater than the angle of the taper of the major portion of the second member.

10. A system according to claim 1 in which the first member has an outer surface configuration which includes a plurality of outwardly extending fins to promote osseointegration with bone material of a living body when received in a recess formed in a bone of the living body.

* * * * *